United States Patent
Li et al.

(10) Patent No.: US 9,333,083 B2
(45) Date of Patent: May 10, 2016

(54) ARTIFICIAL HIP JOINT CONSISTING OF MULTI-LAYER SHELL CORE COMPOSITE STRUCTURAL COMPONENTS

(76) Inventors: Yadong Li, Suzhou (CN); Yajun Li, Suzhou (CN)

( * ) Notice: Subject to any disclaimer, the term of this patent is extended or adjusted under 35 U.S.C. 154(b) by 113 days.

(21) Appl. No.: 13/878,234

(22) PCT Filed: Jun. 30, 2011

(86) PCT No.: PCT/CN2011/076625
§ 371 (c)(1),
(2), (4) Date: Apr. 8, 2013

(87) PCT Pub. No.: WO2012/045248
PCT Pub. Date: Apr. 12, 2012

(65) Prior Publication Data
US 2013/0190889 A1 Jul. 25, 2013

(30) Foreign Application Priority Data
Oct. 8, 2010 (CN) .......................... 2010 1 0299147

(51) Int. Cl.
*A61F 2/34* (2006.01)
*A61F 2/36* (2006.01)
*A61F 2/30* (2006.01)

(52) U.S. Cl.
CPC ................ *A61F 2/3609* (2013.01); *A61F 2/34* (2013.01); *A61F 2002/30011* (2013.01); *A61F 2002/3092* (2013.01); *A61F 2002/30971* (2013.01); *A61F 2310/00011* (2013.01); *A61F 2310/00179* (2013.01); *A61F 2310/00389* (2013.01)

(58) Field of Classification Search
CPC .... A61F 2/34; A61F 2/36; A61F 2002/30971
USPC .................................. 623/22.31, 23.11, 23.36
See application file for complete search history.

(56) References Cited

U.S. PATENT DOCUMENTS 8,257,835 B2 * 9/2012 Jani et al. ...................... 428/689
2011/0264231 A1 * 10/2011 Theillez et al. ............. 623/22.32

OTHER PUBLICATIONS

"Ceramics for Total Hip Replacement", by Guy Annéa, Kim Vanmeenselb, Jef Vleugelsc, Omer Van der Bies td, K.U.Leuven, on Journal of Ceramics, date unknown.

* cited by examiner

*Primary Examiner* — Bruce E Snow
(74) *Attorney, Agent, or Firm* — Kilpatrick Townsend & Stockton LLP

(57) ABSTRACT

An artificial hip joint consisting of multi-layer shell core composite structural components includes an artificial acetabular bone (1) and an artificial femoral head (2) which are mutually matched with each other. The artificial acetabular bone (1) has a multi-layer shell core composite structure and is constituted of a ceramic acetabular bone lining (1-1), transitional layers (1-2, 1-3), an acetabular bone shell made of a porous metal or a porous alloy or a porous toughened ceramic (1-4). The artificial femoral head (2) has a multi-layer shell core composite structure and is constituted of a ceramic spherical shell layer (2-1), a transitional layer (2-5) and a toughened ceramic inner core (2-2). The artificial acetabular bone lining and the artificial femoral head spherical shell layer of the hip joint have high rigid, anti-corrosion and anti-wear performance. The artificial acetabular bone shell layer and the femoral head inner core layer have high tough, shockresistant performance.

6 Claims, 6 Drawing Sheets

ARTIFICIAL HIP JOINT CONSISTING OF MULTI-LAYER SHELL CORE COMPOSITE STRUCTURAL COMPONENTS

CROSS REFERRENCE TO RELATED APPLICATIONS

The present application is a Section 371 National Stage Application of International Application No. PCT/CN2011/076625, filed on Jun. 30, 2011, which claims priority to Chinese patent application No. 201010299147.7, filed on Oct. 8, 2010, and entitled "ARTIFICIAL HIP JOINT CONSISTING OF MULTI-LAYER SHELL CORE COMPOSITE STRUCTURAL COMPONENTS", the entire disclosure of which is incorporated herein by reference.

TECHNICAL FIELD

The present disclosure generally relates to medicine pseudocolloid and an artificial hip joint, and more particularly, to an artificial hip joint composed of two components including an artificial acetabulum having a multilayer shell-core composite structure and an artificial femoral ball head having a multilayer shell-core composite structure.

BACKGROUND

Hip arthroplasty has been an effective way to treat a hip joint trauma, ageing, inflammation and pathological changes, to alleviate patients' pains, to help a patient restore motion ability and to improve patients' living quality. The physical function of an artificial hip joint is achieved through relative motions between an artificial femoral ball head and an artificial acetabulum.

The existing artificial acetabulums typically includes a combinational type and a whole type. A combinational type artificial acetabulum substantially includes a metal acetabular cup (acetabular outer liner) mechanically combined with an Ultra High Molecular Weight Polyethylene (UHMWPE) liner or a ceramic liner. There are small gaps between the metal acetabular cup and the liner, which results in wearing particles due to micro-motion in use. These particles may be swallowed by the macrophage and results in osteolytic factors and further leads to osteolysis around the artificial hip joint, which increases the risk of postoperative complication, such as pain, and collision, dislocation of a femoral ball head, aseptic looseness or sink of the artificial hip joint. Further, during a minimally invasive surgery, it is difficult to install a combined artificial acetabulum due to a narrow operation space.

A whole type artificial acetabulum may overcome problems existing in the above-mentioned combinational artificial acetabulum, such as an insecure combination between the metal acetabular cup and the liner, and unsatisfactory anti-drop and anti-rotation performance. However, the whole type artificial acetabulum including a metal acetabular cup and an UHMWPE liner may limit motion degree of a patient's hip joint due to a high thickness of the UHMWPE as required. An artificial femoral ball head may only have a diameter of about 28 mm. Therefore, an artificial femoral stem (neck) is likely to collide with the edges of the acetabulum, which may result in looseness, and even dislocation of a femoral ball head. A whole type all-metal artificial acetabulum may produce metal ions which are dissolved out due to frictions between the artificial acetabulum and a surface of an artificial femoral ball head. The metal wearing particles (like aluminum, titanium, cobalt or chromium) may be carcinogenic, and may adversely affect the function of the hemopoietic system and intelligence level of the patient. Accordingly, the whole type all-metal artificial acetabulum is not applicable for pregnant women, children, and people who suffer from hematological diseases or hepatic and renal dysfunction. A whole type all-ceramic artificial acetabulum has an excellent histocompatibility, without releasing of potentially toxic metal ions and together with a high surface hardness and excellent wear resistance; however, the ceramic still has drawbacks such as low fracture toughness, bad impact-resistance bearing capacity, and insecurity in biomedical application.

So far, there is no effective method to avoid the problems of wearing particles, dissolution of metal ions and brittle fracture in the existing artificial acetabulum during the biomedical application.

For a long time, cobalt-based or titanium-based alloy has been widely used as a material of the artificial femoral ball head. However, problems same as the whole type all-metal artificial acetabulum mentioned above still exist. To solve the problems, both U.S. Pat. No. 6,241,773 and Japanese patent No. 2579212 disclosed an artificial femoral ball head made of high-purity aluminia ceramic. However, the aluminia ceramic has disadvantages of high brittleness, low fracture toughness, and had impact-resistance bearing capacity. The aluminia ceramic femoral ball head is likely to fracture in vivo. Accordingly, the aluminia ceramic itself is not an ideal material for each component of an artificial hip joint. Chinese patent application No. CN1386067A, filed by Matsushita Electric Industrial Co., Ltd. in 2005, discloses an artificial hip joint made of composite ceramic including zirconia-aluminia. The composite ceramic includes a matrix-phase of zirconia in a tetragonal crystal structure and a second-phase of aluminia particles dispersed the matrix-phase. Compared with the high-purity aluminia, the problems of fracture toughness is improved significantly, however, the mechanical strength (hardness), wear resistance and stability of phases are decreased, which may not support a durable and stable hip joint movement in a human body. Therefore, there is still a huge gap between the existing artificial hip joint and the desire of lifetime service, and it is far from meeting requirements of the majority of patients.

SUMMARY

The present disclosure provides an artificial hip joint composed of multilayer shell-core composite structural components, which fundamentally avoids aseptic loosening or sinking, metal ions allergy, dislocation and brittle fracture of a femoral ball head resulted from wearing particles generated on a surface of a movable joint while using a conventional artificial hip joint. The artificial hip joint according to the disclosure may have advantages of long lifetime, and good matching ability and stability of performance, and may decrease the risk of a reoperation.

In one embodiment of the present disclosure, an artificial hip joint composed of multilayer shell-core composite structural components may include: an artificial acetabulum and an artificial femoral ball head which are mutually matched with each other, where the artificial acetabulum has a multilayer shell-core composite structure including a ceramic acetabular liner, a transition layer and an acetabular shell made of a porous metal, a porous alloy or a porous toughened ceramic, and the artificial femoral ball head has a multilayer shell-core composite structure including a ceramic spherical shell layer, a transition layer and a toughened ceramic inner core.

In the embodiment, the hip joint is composed of two kinds of sliding fit components including an artificial acetabulum having a multilayer shell-core composite structure and an artificial femoral ball head having a multilayer shell-core composite structure. The artificial acetabulum having a multilayer shell-core composite structure is a whole type artificial acetabulum, which has a multiple-layer structure including a shell layer, a transition layer and an inner (core) layer (acetabular liner), where the inner layer is made of ceramic, the shell layer is made of a porous metal (alloy) or a porous toughened ceramic. The artificial acetabulum having a multilayer shell-core composite structure is manufactured through elevated temperature sintering, which may result in a ceramic acetabular liner having properties of high hardness (HV>1900), high wear resistance, high corrosion resistance and a smooth finished surface, and a porous metal (alloy) or a porous toughened ceramic shell layer having properties of a high fracture toughness ($K_{IC}$>10 MPa·m$^{-1/2}$), a high flexural strength, a high load bearing capacity. Meanwhile, the acetabulum has high adhesive strength between the shell layer and the inner layer.

The porous metal (alloy) or the porous toughened ceramic of the artificial acetabular shell layer may have a pore structure and a pore profile similar to a cancellous bone. It has a three-dimensional porosity ranging from 50% to 80%, and a pore diameter ranging from about 50 μm to 250 μm, which are beneficial for inducing an ingrowth of bone tissues and vessels to obtain an extensive bone support. The pore structure which is connected three dimensionally contributes to a rapid ingrowth of the bone tissues to form a robust adhesion, so as to obtain high shear strength of an interface of the bone tissues, which thereby benefits a long-term stability of the artificial acetabulum. Further, the porous metal (alloy) or the porous toughened ceramic not only is biocompatible, but also has an elasticity modulus more similar to the cancellous bone.

In the embodiment, the artificial femoral ball head includes a ceramic shell layer, a transition layer and a toughened ceramic core. The artificial femoral ball head has a multilayer shell-core composite structure manufactured through high heat sintering, which may result in a ceramic shell layer having properties of high hardness (HV>1900), high wear resistance, high corrosion resistance and a high surface finish, and a toughened ceramic core of composite structure having properties of a high fracture toughness ($K_{IC}$>10 MPa·m$^{-1/2}$), a high flexural strength, a high load bearing capacity. Both the ceramic shell layer and the core have advantages of a high adhesive strength, high mechanical bearing capacity, and high matching ability and stability of performance.

According to the property of materials actually being used and the requirement of the multilayer shell-core composite structure, the transition layer of the artificial acetabulum may have a single-layer or multi-layer structure, and the transition layer of the artificial femoral ball head may have a single-layer or multi-layer structure. The multi-layer structure of a transition layer may improve the matching performances in physical, chemical and mechanical properties between the acetabular liner and the acetabular shell, and between the artificial femoral ball head shell layer and the inner core, so as to decrease an interlayer interface stress and to increase an interlayer adhesive strength.

In some embodiments, each layer may have a thickness of about 0.1 mm to about 20 mm.

In some embodiments, the transition layer of the artificial acetabulum may adopt a composite material obtained through sintering a mixed powder including the acetabular liner material and the acetabular shell material. The transition layer of the artificial femoral ball head may adopt a composite material obtained through sintering a mixed powder including the shell layer material and the inner core material.

Both the acetabular liner and the artificial femoral ball head may have a multi layer shell-core composite structure manufactured by sintering a green body obtained using a powder injection molding process. The ceramics employed may include: superfine aluminium oxide, zirconium oxide, chromium carbide, silicon nitride, silicon carbide, titanium carbide, zirconium carbide, zirconium nitride, tantalum carbide, tungsten carbide, or a compound of the above-mentioned oxide ceramic or nonoxide ceramic, where the ceramic is formed through sintering. The metal or alloy employed may include: niobium, zirconium, titanium, tantalum, cobalt, molybdenum, vanadium, chromium, aluminum, magnesium, or a compound of the above-mentioned metal or a stainless steel powder, where the metal or alloy is formed through sintering. The toughened ceramics may be a metal-based or ceramic-based metal; ceramic assembly formed by the above-mentioned metal and ceramic, or ceramic toughened by zirconia, whisker or fiber.

In some embodiments, multiple-head convex or concave screw thread may be disposed on a surface of the acetabular shell, which may increase the contact area between the artificial acetabular shell and the bone tissue, generate a high grasping force, and transform a shear force between the acetabulum and the bone tissue into a pressure stress, so that the artificial acetabulum's stability when it is implanted at an initial stage and the success rates of the hip arthroplasty can be increased.

Compared with the conventional technology, the present disclosure has the following advantages:

1. The artificial acetabulum according to embodiments of the present disclosure has a multilayer shell-core composite structure. Compared with the existing whole type artificial acetabulum, the acetabular liner of the present disclosure employs a ceramic material having high hardness and wear resistance, and the acetabular liner may significantly decrease its thickness. Therefore, an artificial femoral ball head having a diameter of 36 mm or even greater may be used for increasing service lifetime of the artificial femoral ball head, an artificial acetabulum formed thereof may decrease risk of colliding and dislocation significantly, and a patient's hip joint may have a larger motion degree, which are hard for the existing conventional combinational type or whole type artificial acetabulums to obtain.

2. According to embodiments of the present disclosure, a porous metal (alloy) or a porous toughened ceramic is adopted for a shell layer of the artificial acetabulum having a multilayer shell-core composite structure, and multiple-head convex or concave screw thread are disposed on the shell surface, which may ensure an excellent synosteosis between the artificial acetabulum and the bone tissue, further increase contact areas between the artificial acetabulum and the bone tissue, and thereby increase the artificial acetabulum's stability when it is implanted at an initial stage.

3. The artificial femoral ball head having a multilayer shell-core composite structure according to embodiments of the present disclosure may avoid a sudden fracture risk which is likely to occur in the conventional ceramic femoral ball head due to its brittleness in biomedical application. Further, it may also overcome defects of a low surface hardness, low wear resistance, and low phase stability in the conventional zirconia-aluminia composite ceramic artificial femoral ball head (compared with an aluminia artificial femoral ball head), and a difficulty to support a durable and stable joint movement in a human body.

4. The artificial hip joint composed of multilayer shell-core composite structural components according to embodiments of the present disclosure has an excellent histocompatibility, significantly decreases generation of wearing particles, and prevent phenomenon of releasing potentially toxic metal ions, and an aseptic loosening or sinking of the artificial hip joint. The artificial acetabulum and the artificial femoral ball head have a high surface hardness and good wear resistance, which may resist an abrasive wear and a third body friction wear. The artificial acetabulum and the artificial femoral ball head have a high flexural strength, a high fracture toughness, and a high load bearing capacity. Further, movable surfaces of a ceramic joint formed by the artificial acetabulum and the artificial femoral ball head has a good hydrophily, which may maintain lubrication on the friction surface and decrease an adhesive wear, which is much suitable for young patients or patients practicing heavy exercises. Further, it has excellent mechanical bearing capacity, durability and stability of performance.

DETAILED DESCRIPTION

Hereinafter, the disclosure will be described in detail with several embodiments in conjunction with the accompanying drawings.

Figure 1:
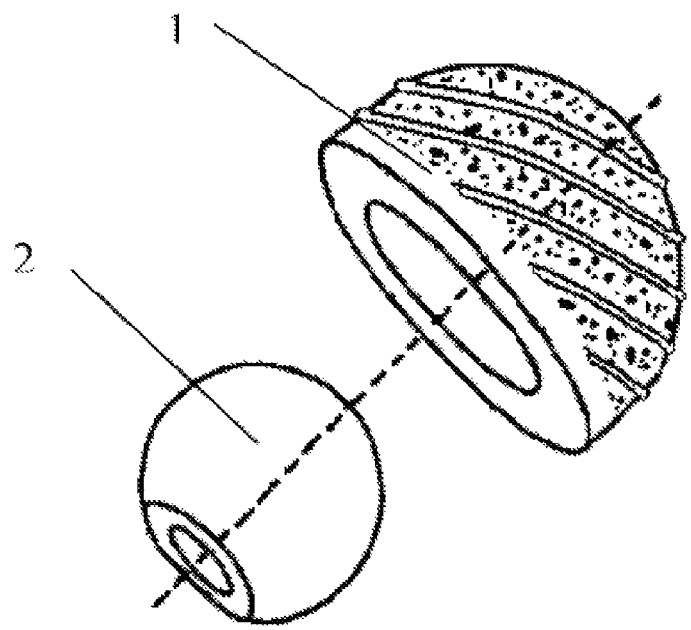
FIG. 1 and FIG. 2 schematically illustrate exploded perspective views of two kinds of artificial hip joints composed of multilayer shell-core composite structural components according to embodiments of the present disclosure.
Figure 2:
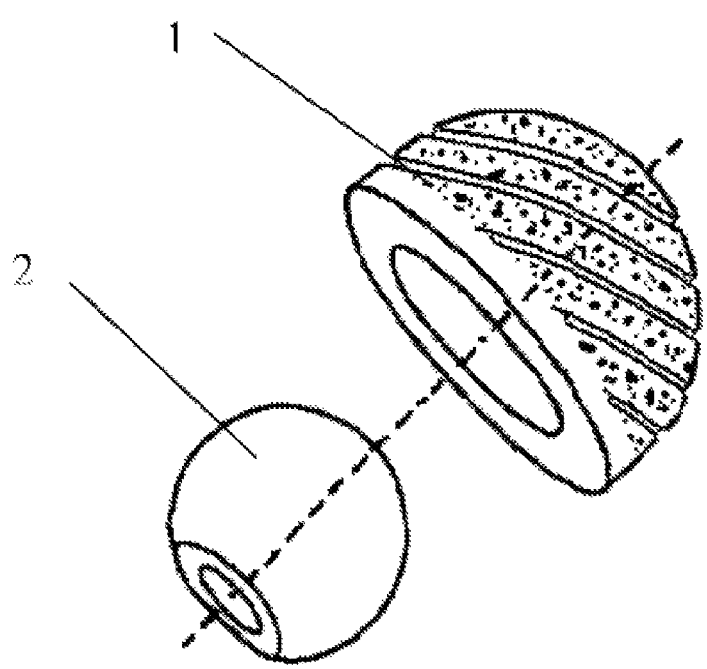

FIG. 1 and FIG. 2 schematically illustrate exploded perspective views of two kinds of artificial hip joints composed of multilayer shell-core composite structural components according to embodiments of the present disclosure. Both of the two kinds of artificial hip joints include an artificial acetabulum 1 having a multilayer shell-core composite structure and an artificial femoral ball head 2 having a multilayer shell-core composite structure. The artificial acetabulum 1 has two kinds of structures: multiple-head convex screw thread (shown in FIG. 1) or multiple-head concave screw thread (shown in FIG. 2) disposed on a surface of a shell 1-4, which may be selected based on actual requirements. The artificial acetabulum 1 and the artificial femoral ball head 2 constitute a movable joint, thanks to a concave sphere of an artificial acetabular liner layer 1-1 and a sphere of an artificial femoral ball head shell layer 2-1 being fit slidingly. The concave sphere of the artificial acetabular liner layer 1-1 and the sphere of the artificial femoral ball head shell layer 2-1 are processed into mirror surfaces and can slide freely relative to each other. When the artificial hip joint is implanted, the artificial acetabulum 1 is fixed at the location of the original acetabulum of the human body, and the artificial femoral ball head 2 is fixed at a neck of the artificial femoral stem which is matched with femoral medullary cavity. Then, the artificial femoral ball head 2 is mounted in the artificial acetabular liner layer 1-1, so as to achieve physical function of the artificial hip joint.

Embodiment One

Figure 3:
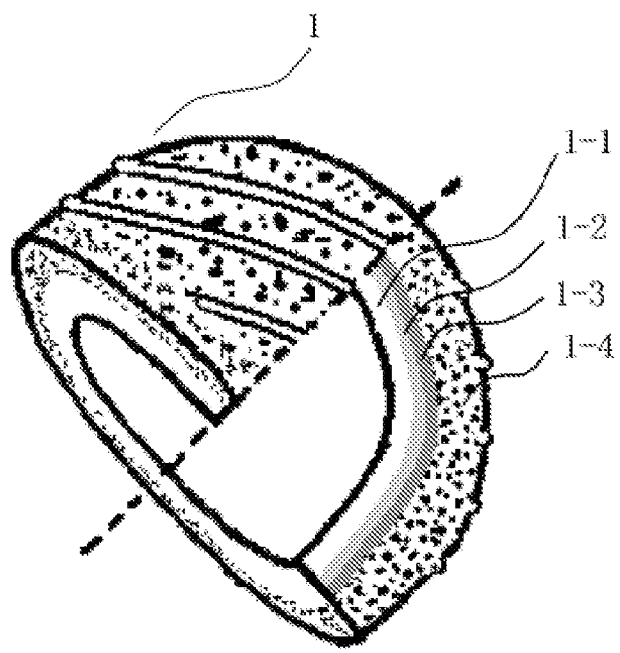
FIG. 3 and FIG. 4 schematically illustrate part cross-sectional views of two kinds of artificial acetabulums having a multilayer shell-core composite structure which has multiple-head convex screw thread disposed thereon according to embodiments of the present disclosure.
Figure 4:
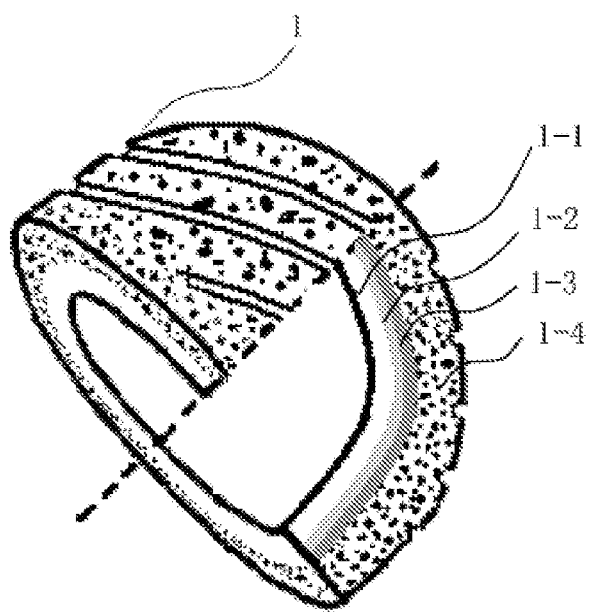

An artificial acetabulum having a multilayer shell-core composite structure in an artificial hip joint composed of multilayer shell-core composite structural components, includes an acetabular liner layer 1-1 made of high-purity and superfine alumina ceramic, a transition layer 1-2 made of alumina-based (25 vol % niobium) cermet, a transition layer 1-3 made of alumina-based (65 vol % niobium) cermet, and a metal shell layer 1-4 made of niobium porous. Multiple-head convex screw thread (shown in FIG. 3) or multiple-head concave screw thread (shown in FIG. 4) may be disposed on a surface of the shell layer 1-4, which may be selected based on actual requirements. The high-purity and superfine alumina powder may have a purity greater than 99.9 wt %, and have a particle size ranging from 0.5 μm to 10 μm. The niobium metal powder may have a purity greater than 99.8 wt %, and have a particle size ranging from 0.5 μm to 20 μm. All of the acetabular liner layer 1-1 made of high-purity and superfine alumina ceramic, the transition layer 1-2 made of alumina-based (25 vol % niobium) cermet, the transition layer 1-3 made of alumina-based (65 vol % niobium) cermet, and the metal shell layer 1-4 made of niobium porous are injection molded into one piece layer by layer using multi-material powder co-injection molding. The liner layer 1-1, the transition layers 1-2 and 1-3, and the shell layer 1-4 are overlapped parallelly at the edges of an acetabulum opening.

Embodiment Two

Figure 5:
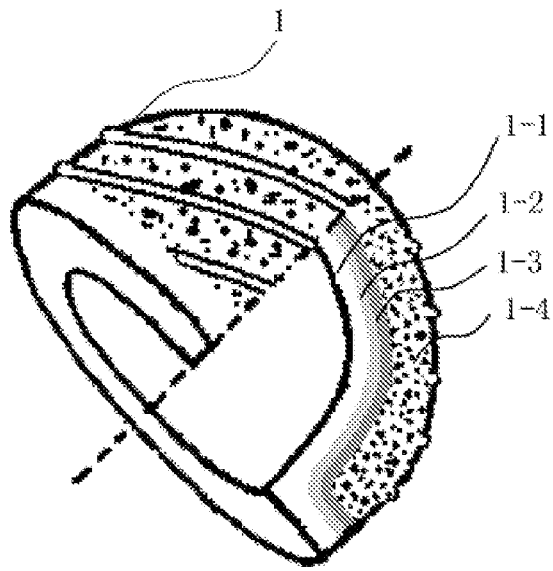
FIG. 5 and FIG. 6 schematically illustrate part cross-sectional views of two kinds of artificial acetabulums having a multilayer shell-core composite structure which has multiple-head concave screw thread disposed thereon according to embodiments of the present disclosure.
Figure 6:
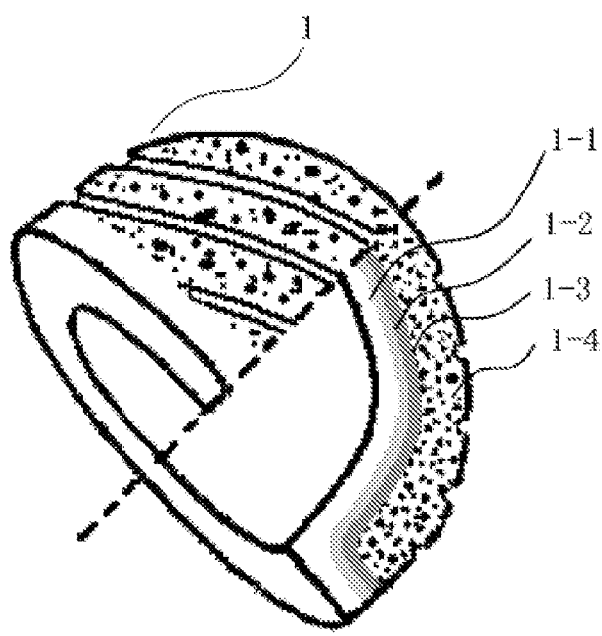
Figure 7:
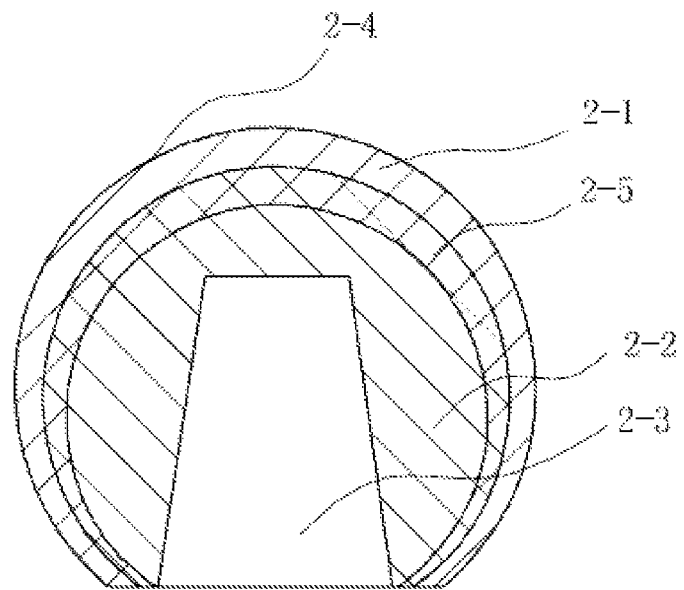
FIG. 7 to FIG. 11 schematically illustrate cross-sectional views of five kinds of artificial femoral ball heads composed of multilayer shell-core composite structural components according to embodiments of the present disclosure.
Figure 8:
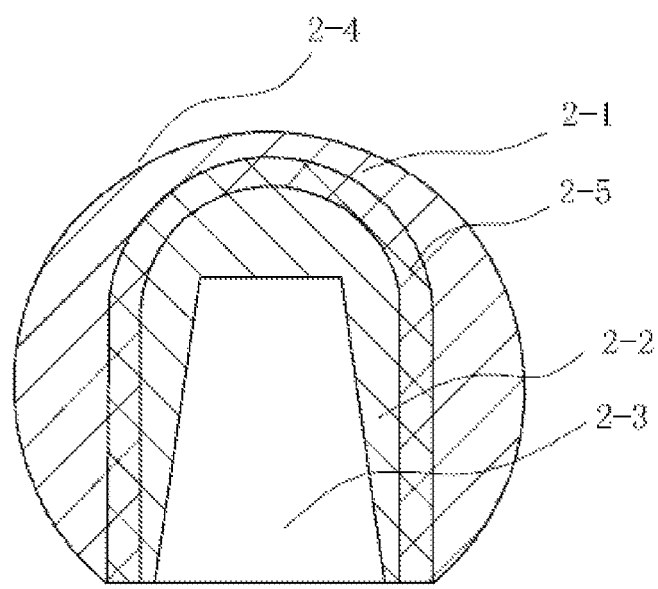
Figure 9:
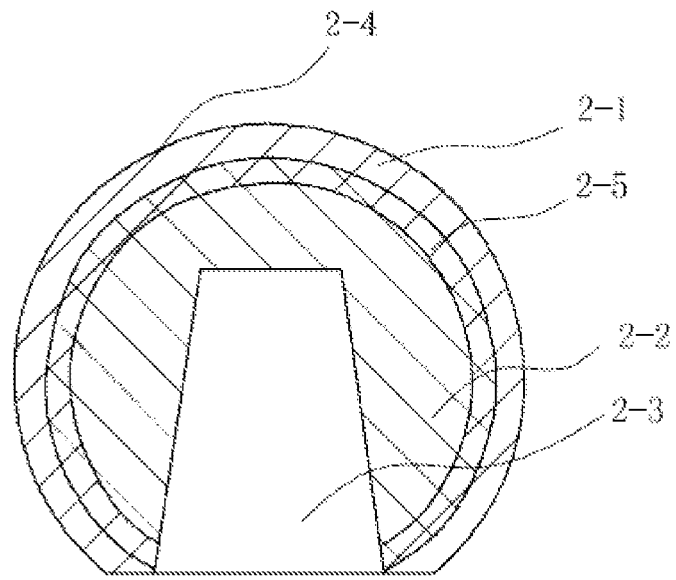
Figure 10:
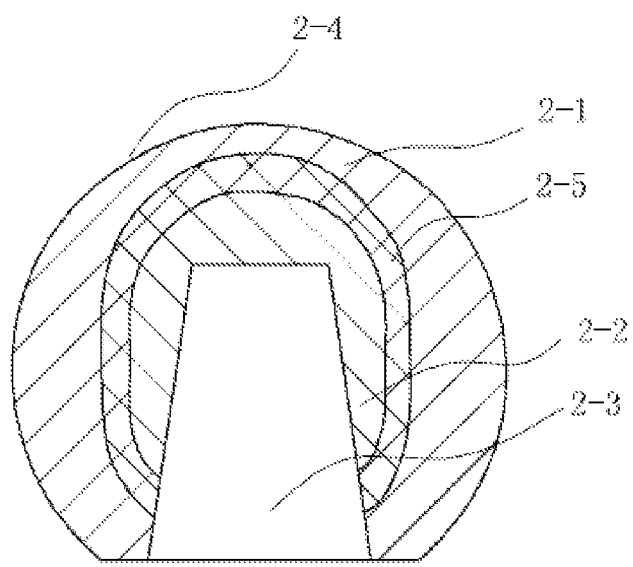
Figure 11:
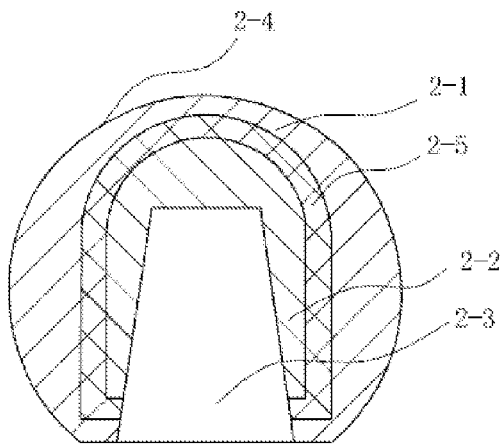

An artificial acetabulum having a multilayer shell-core composite structure in an artificial hip joint composed of multilayer shell-core composite structural components, includes an acetabular liner layer 1-1 made of high-purity and superfine alumina ceramic, a transition layer 1-2 made of Ti6Al4V-60 vol. % $Al_2O_3$, a transition layer 1-3 made of Ti6Al4V-20 vol. % $Al_2O_3$, and a shell layer 1-4 made of Ti6Al4V. Multiple-head convex screw thread (shown in FIG. 5) or multiple-head concave screw thread (shown in FIG. 6) may be disposed on a surface of the shell layer 1-4, which may be selected based on actual requirements. The high-purity and superfine alumina powder may have a purity greater than 99.9 wt %, and have a particle size ranging from 0.5 μm to 10 μm. The Ti6Al4V powder may have a purity greater than 99.0 wt %, and have a particle size ranging from 5 μm to 25 μm. All of the acetabular liner layer 1-1 made of high-purity and superfine alumina ceramic, the transition layer 1-2 made of Ti6Al4V-60 vol. % $Al_2O_3$, the transition layer 1-3 made of Ti6Al4V-20 vol. % $Al_2O_3$, and the shell layer 1-4 made of Ti6Al4V are injection molded into one piece layer by layer using multi-material powder co-injection molding. The acetabular liner layer 1-1 made of high-purity and superfine alumina. ceramic fully covers the transition layers 1-2 and 1-3 and the shell layer 1-4.

Embodiment Three

An artificial femoral ball head having a multilayer shell-core composite structure in an artificial hip joint composed of multilayer shell-core composite structural components, includes a spherical shell layer 2-1 made of high-purity and superfine alumina ceramic, a transition layer 2-5 made of $ZrO_2$ $(3Y_2O_3)$-80 wt. % $Al_2O_3$ toughened ceramic, and an inner care 2-2 made of $ZrO_2(3Y_2O_3)$-20 wt. % $Al_2O_3$ toughened ceramic. The high-purity and superfine alumina powder may have a purity greater than 99.9 wt %, and have a particle size ranging from 0.5 m to 10 µm. The $ZrO_2$ powder may have a purity greater than 99.8 wt %, and have a particle size ranging from 0.5 µm to 10 µm. All of the spherical shell layer 2-1 made of high-purity and superfine alumina ceramic, the transition layer 2-5 made of $ZrO_2$ $(3Y_2O_3)$-80 wt. % $Al_2O_3$ toughened ceramic, and the inner core 2-2 made of $ZrO_2$ $(3Y_2O_3)$-20 wt. % $Al_2O_3$ toughened ceramic are injection molded into one piece layer by layer using multi-material powder co-injection molding. Five kinds of multilayer shell-core composite structures are illustrated in FIG. 7 to FIG. 11, which may be selected based on actual requirements.

Figure 12:
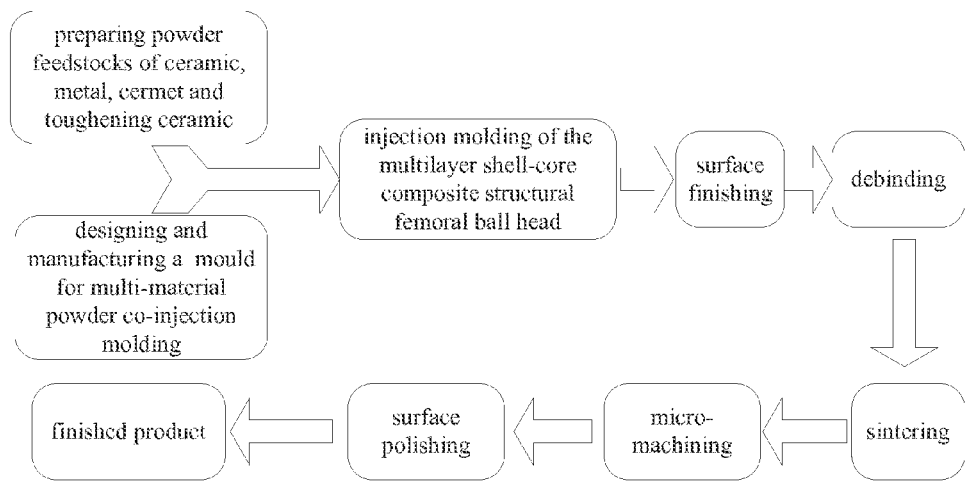
FIG. 12 schematically illustrates a flow chart of a method for manufacturing an artificial femoral ball head according to an embodiment of the present disclosure.

Referring to FIG. 12, a method for manufacturing an artificial femoral ball head according to an embodiment of the present disclosure may include: (1) preparing feedstocks for powder injection molding which include high-purity and superfine aluminia powder, toughened ceramic compound powder of $ZrO_2$ $(3Y_2O_3)$-80 wt. % $Al_2O_3$, and toughened ceramic powder of $ZrO_2$ $(3Y_2O_3)$-20 wt. % $Al_2O_3$. The prepared powders are mixed with polyoxymethylene resin binder (89 wt. % polyformaldehyde, 5 wt. % high density polyethylene and 6 wt. % other binding assistant agent). The mixture is then mixed at a temperature of about 180° C. for about two and a half hours, so that a polyaldehydes system is obtained, which has a solid loading greater than 55 vol. %.

(2) by using three sets of moulds, performing injection molding successively to obtain an inner core, a transition layer and a. spherical shell layer, so as to obtain a green body of the femoral ball head having a multilayer shell-core composite structure. The temperature of the injection may be in a range from about 170 to 180° C., the pressure of the injection may be in a range from about 110 MPa to 130 MPa, the dwell pressure may be in a range from about 70 MPa to 80 MPa, and the cooling time may be in a range from about 3 minutes to 4 minutes.

(3) if necessary, performing surface finishing on a surface of the spherical shell and a bore-hole in the inner core of the green body of the femoral ball head having a multilayer shell-core composite structure.

(4) performing catalytic debinding on the green body of the femoral ball head having a multilayer shell-core composite structure in an atmosphere furnace with a temperature ranging from about 110° C. to about 120° C. where hydrogen nitrate is used as a debinding catalyst, nitrogen is used as a debinding carrier gas, and the catalytic debinding may last for about 5 hours.

(5) after being catalytically debound, sintering the green body of the femoral ball head having a multilayer shell-core composite structure in a controlled atmosphere Hot Isostatic Pressing (HIP) furnace, where the sintering may be performed at a temperature of about 1450° C., a pressure of about 35 MPa, and the soaking time is about 1 hour.

(6) according to size requirements of the products, performing micro-machining on the surface of the spherical shell and the bore-hole of the sintered body.

(7) then, polishing the surface of the spherical shell by using SiC ultrafine powder and diamond abrasive paste, to obtain the femoral ball head having a multilayer shell-core composite structure, which has a smooth finished surface, and a proper dimensional coordination between the bore-hole and the femoral stem.

Embodiment Four

An artificial femoral ball head having a multilayer shell-core composite structure in an artificial hip joint composed of multilayer shell-core composite structural components, includes a spherical shell layer 2-1 made of high-purity and superfine alumina ceramic, a transition layer 2-5 made of $Al_2O_3$-30 vol % Ce-TZP) toughened ceramic, and an inner core 2-2 made of $Al_2O_3$-70 vol % E Ce-TZP) toughened ceramic. The high-purity and superfine alumina powder may have a purity greater than 99.9 wt %, and have a particle size ranging from 0.5 µm to 10 µm. The $ZrO_2$ powder may have a purity greater than 99.8 wt %, and have a particle size ranging from 0.5 µm to 10 µm. All of the spherical shell layer 2-1 made of high-purity and superfine alumina ceramic, the transition layer 2-5 made of $Al_2O_3$-30 vol % (Ce-TZP) toughened ceramic, and the inner core 2-2 made of $Al_2O_3$-70 vol % (Ce-TZP) toughened ceramic are injection molded into one piece layer by layer using multi-material powder co-injection molding. Five kinds of multilayer shell-core composite structures are illustrated in FIG. 7 to FIG. 11, which may be selected based on actual requirements.

Although the present disclosure has been disclosed above with reference to preferred embodiments thereof, it should be understood that the disclosure is presented by way of example only, and not limitation. Those skilled in the art can modify and vary the embodiments without departing from the spirit and scope of the present disclosure.

What is claimed is:

1. An artificial hip joint composed of multilayer shell-core composite structural components, comprising: an artificial acetabulum and an artificial femoral ball head which are mutually matched with each other, where the artificial acetabulum has a multilayer shell-core composite structure, which comprises a ceramic acetabular liner, a transition layer and an acetabular shell which is adapted to contact with a human body; the artificial acetabulum is manufactured through sintering a green body of successively stacked layers of the ceramic acetabular liner, the transition layer and the acetabular shell, and the green body of successively stacked layers of the ceramic acetabular liner, the transition layer and the acetabular shell is obtained through a powder co-injection molding process; the acetabular shell is made of a porous toughened ceramic; the ceramic acetabular liner is made of ceramic material; and the transition layer of the artificial acetabulum is made of composite material comprising materials of the shell layer and the acetabular liner of the artificial acetabulum;

where the artificial femoral ball head has a multilayer shell-core composite structure, which comprises a ceramic spherical shell layer, a transition layer and a toughened ceramic inner core; the artificial femoral ball head is manufactured through sintering a green body of successively stacked layers of the ceramic spherical shell layer, the transition layer and the toughened ceramic inner core, and the green body of successively stacked layers of the ceramic spherical shell layer, the transition layer and the toughened ceramic inner core is obtained through a powder co-injection molding process; the toughened ceramic inner core is made of toughened ceramic; the ceramic spherical shell layer is made of ceramic material; and the transition layer of the femoral ball head is made of composite materials comprising materials of the toughened ceramic inner core and the ceramic spherical shell layer of the femoral ball head.

2. The artificial hip joint according to claim 1, where the transition layer of the artificial acetabulum has a single-layer or multi-layer structure, and the transition layer of the artificial femoral ball head has a single-layer or multi-layer structure.

3. The artificial hip joint according to claim 1, where multiple convex and concave screw thread are disposed on a surface of the acetabular shell.

4. The artificial hip joint according to claim 1, where a three-dimensional porosity of the porous toughened ceramic ranges from 50% to 80% in the acetabular shell, a pore diameter of the porous toughened ceramic ranges from 50 μm to 250 μm, and a pore structure of the porous toughened ceramic is connected three dimensionally.

5. The artificial hip joint according to claim 1, where the ceramic acetabular liner, the transition layer and the acetabular shell are overlapped parallelly at the edges of an acetabulum opening, or the ceramic acetabular liner fully covers the transition layer and the acetabular shell.

6. The artificial hip joint according to claim 1, where the spherical shell layer of the artificial ball head is made of high-purity and superfine alumina ceramic, the transition layer of the artificial ball head is made of toughened ceramic comprising $ZrO_2$ $(3Y_2O_3)$ and $Al_2O_3$, and the toughened ceramic inner core of the artificial ball head is made of toughened ceramic comprising $ZrO_2$ $(3Y_2O_3)$ and $Al_2O_3$; or, the spherical shell layer is made of high-purity and superfine alumina ceramic, the transition layer is made of toughened ceramic comprising $Al_2O_3$ and Ce-TZP, and the toughened ceramic inner core is made of toughened ceramic comprising $Al_2O_3$ and Ce-TZP.

* * * * *